United States Patent
Terry et al.

(10) Patent No.: US 6,280,469 B1
(45) Date of Patent: Aug. 28, 2001

(54) IMPLANTABLE IRIS DEVICE FOR THE EYE, AND METHOD OF INSTALLING SAME

(76) Inventors: Mark A. Terry, 318 NW. Lomita Ter., Portland, OR (US) 97210; Paula J. Ousley, 3414 SE. Harold Ct., Portland, OR (US) 97202

( * ) Notice: Subject to any disclaimer, the term of this patent is extended or adjusted under 35 U.S.C. 154(b) by 0 days.

(21) Appl. No.: 09/309,746

(22) Filed: May 11, 1999

(51) Int. Cl.$^7$ ................................................. A61F 2/14
(52) U.S. Cl. .............................................. 623/4.1; 623/905
(58) Field of Search .................... 623/4.1, 905, FOR 103

(56) References Cited

U.S. PATENT DOCUMENTS

| | | |
|---|---|---|
| Re. 34,998 | 7/1995 | Langerman . |
| 4,888,016 | 12/1989 | Langerman . |
| 5,196,026 | 3/1993 | Barrett et al. . |
| 5,472,436 | 12/1995 | Fremstad . |

FOREIGN PATENT DOCUMENTS

| | | | |
|---|---|---|---|
| DE 3926536 | 2/1991 | (DE) . | |
| 2 696 340 A1 | * 4/1994 | (FR) | ............................ 623/FOR 103 |
| 2 728 459 A1 | * 6/1996 | (FR) | ............................ 623/FOR 105 |

OTHER PUBLICATIONS

Pigmented Corneal Implants: A Surgical Treatment for Iridectomy Related Optical Complications, Annals of Ophthalmology, Mar. 1983, pp. 205–207.

Management of Monocular Polyopia Using an Artificial Iris Contant Lens, Journal of the American Optometric Association, vol. 59, No. 2, Feb. 1988, pp. 140–142.

Elimination of Monocular Diplopia by Corneal Tattooing, Ophthalmic Surgery, vol. 19, No. 6, Jun. 1988, pp. 437–439.

Artificial Iris Diaphragm and Silicone Oil Surgery, Retina, vol. 12, No. 3S, 1992, pp. S90–S94.

(List continued on next page.)

Primary Examiner—David H. Willse
(74) Attorney, Agent, or Firm—Kolisch, Hartwell, Dickinson, McCormack & Heuser

(57) ABSTRACT

An implantable artificial iris device which takes the form of a thin, generally annular, single-radially-split wafer, or web, of a bio-compatible, flexible material which can be colored in various ways to replicate the appearance of its predecessor, damaged natural iris. The device permits and encourages a surgical procedure which involves gentle and very simple circular threading (or snaking) of the device circularly longitudinally through a tiny slit created as an incision near the periphery of a cornea. The device is suitable for easy placement within the environment of an eye, either within the region known as the ciliary sulcus or in the region of meeting or joinder of the anterior and posterior capsules and within the realm of the capsular bag.

8 Claims, 3 Drawing Sheets

OTHER PUBLICATIONS

Soft Opaque Contact Lenses in Binocular Vision Problems, Journal of the American Optometric Association, vol. 64, No. 3, Mar. 1993, pp. 176–180.

Corneal Tattooing to Reduce Glare in Cases of Traumatic Iris Loss, Cornea, vol. 13, No. 5, 1994, pp. 401–405.

Black–Diaphragm Intraocular Lens for Correction of Aniridia, Ophthalmic Surgery, vol. 25, No. 3, Mar. 1994, pp. 180–185.

Reconstruction of the Anterior and Posterior Segment of the Eye After Massive Injury, German Journal of Ophthalmology, 3:84–89, 1994.

Black Diaphragm Intraocular Lens in Congenital Aniridia, German Journal of Ophthalmology, 3:197–201, 1994.

Frosted–Iris Intraocular Lens for Traumatic Aniridia with Cataract, Ophthalmic Surgery, vol. 25, No. 10, Nov./Dec. 1994, pp. 730–731.

Vitreoretinal Surgery and Technology, The Newsletter of Vitreoretinal Surgeons, Special Issue, vol. 8, No. 3, Summer/Fall 1996, pp. 1–5.

The Artificial Iris Diaphragm for Vitreoretinal Silicone Oil Surgery, Retina, The Journal of Retinal and Vitreous Diseases, vol. 17, No. 4, 1997, pp. 330–337.

Prosthetic Contact Lenses Normalize Disfigured Eyes, Ophthamology Times, Cornea Special Section, Jan. 15, 1998, p. 18.

Lamellar Intrastromal Corneal Tattoo for Treating Iris Defects (Artificial Iris), Cornea, vol. 17, No. 2, 1998, pp. 169–173.

A New Treatment for Photophobia in Posttraumatic Aniridia; A Case Report, Cornea, vol. 17, No. 3, 1998, pp. 338–341.

Information on the Aniridia—IOL, 4 pages, Morcher GmbH, Stuttgart, Germany.

Aniridia Type 50C Ring Replaces Damaged, Atrophic Iris, Ocular Surgery News, Jan. 1999, 3 pages.

* cited by examiner

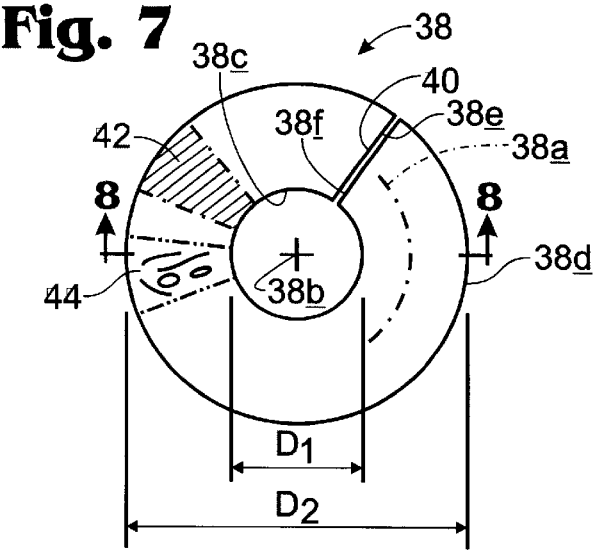
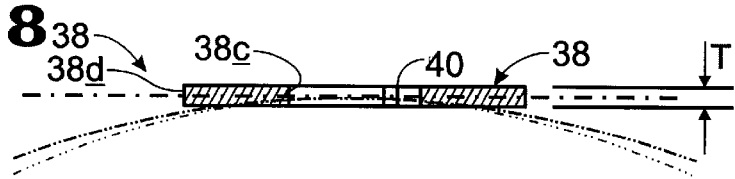
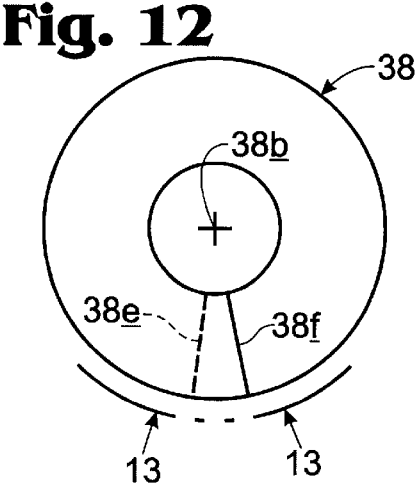
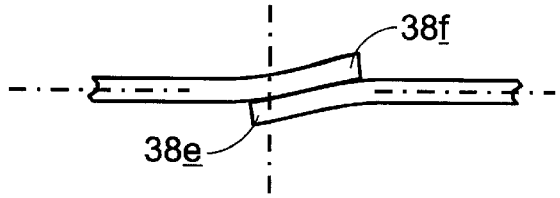

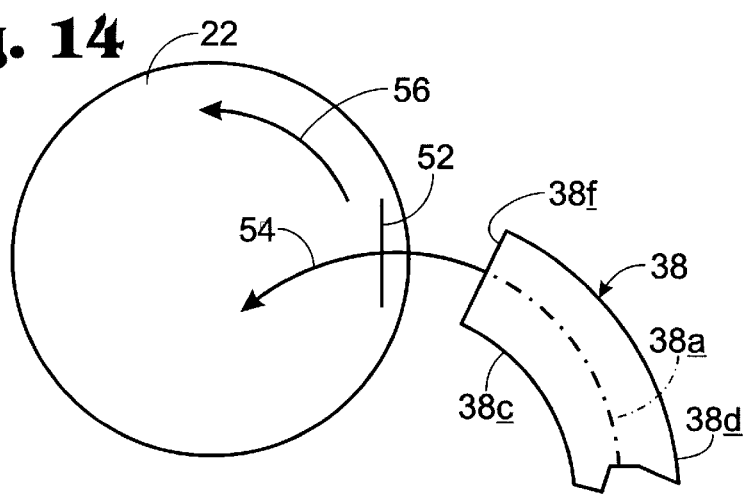
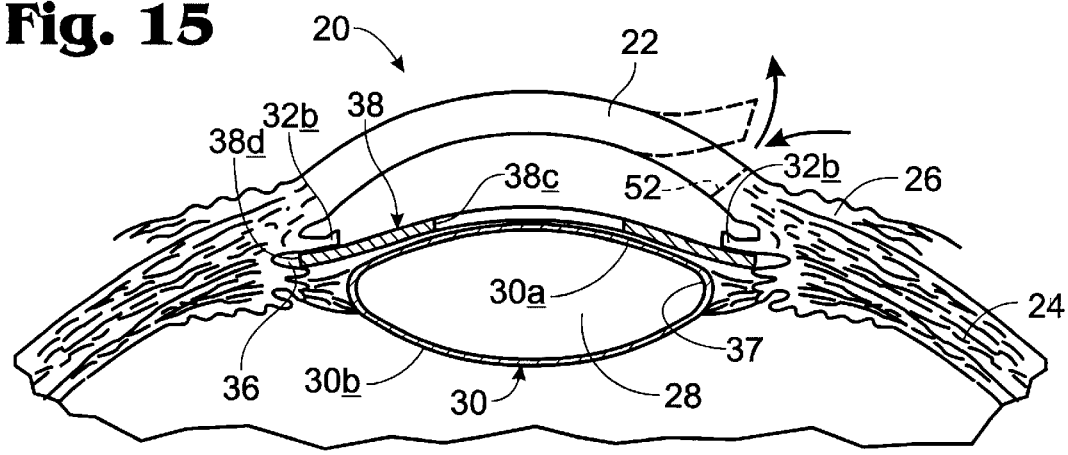
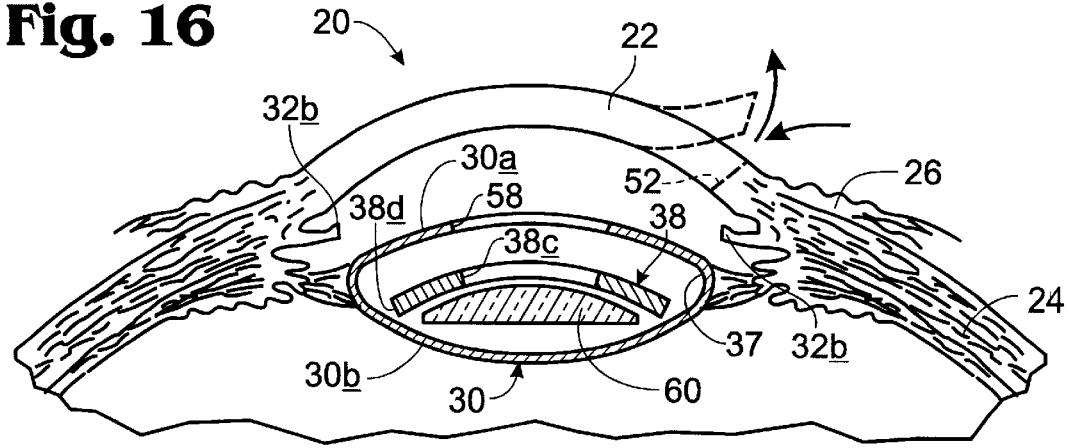

IMPLANTABLE IRIS DEVICE FOR THE EYE, AND METHOD OF INSTALLING SAME

BACKGROUND AND SUMMARY OF THE INVENTION

This invention relates generally to the art of ophthalmic surgery devices and procedures relating to "repair" of a damaged natural iris. The word "repair" herein is employed to refer both to iris-replacement and iris-augmentation. More particularly, it pertains to a novel artificial iris device, and to a unique surgical method for installing and positioning that device in a subject's eye to replace all or a part of a damaged iris. The term "subject" is used herein principally to refer to a human subject, but those skilled in the art will recognize that the new features of this invention are relevant also to animals.

Several forms of devices made in accordance with the present invention, and several surgical approaches employed to utilize these devices, are described and illustrated herein, with focus given particularly to the installation of such a device either within the ciliary sulcus in a selected eye, or immediately in front of an artificial lens and within the capsular bag in an eye.

In general terms, the artificial iris device of the present invention takes the form of a relatively thin (typically in the range of about 0.1- to about 0.3-millimeters), flexible, bio-compatible web or expanse of a suitable material, such as a silicone material, formed generally with a body-of-revolution annular flat, generally washer-like configuration having inner and outer diameters selected, as will be explained, to "match" certain natural dimensional characteristics of a selected eye wherein the device is to be employed. The body of the proposed device has a generally radially extending slit (radially, that is, relative to the central, axis of revolution of the device) which extends completely from the inside diameter to the outside diameter at one location in the device, thus to give the device a split-ring-like quality. Typically, the nominal outside diameter will be sized so that, depending upon where the device is to be positioned in an eye, it is about the same as, or just slightly less than, either (1) the outside (internal) diameter of the ciliary sulcus, or (2)—therefor the outside diameter of the interior of the inside perimeter of the capsular bag. This dimension, generally, is somewhere the vicinity of about 10-millimeters, give or take whatever is necessary to fit the device into its intended ultimate placement location. The nominal inside diameter of the device, which inside diameter defines a nominal artificial pupil opening, is typically in the range of about 3- to about 4-millimeters.

The radially inner and radially outer edges in the device are preferably smooth and substantially circular, and the expanse, or main body, in the device is preferably either light-opaque or slightly light-transmissive (particularly in the region adjacent the device's inner edge). Further, the body in the device preferably is suitably colored (by any appropriate conventional technique) so that it will substantially match the color appearance of the natural iris with respect to which it is to be employed. This color may either be a selected uniform color or, probably more preferably, a variegated color, which variegation generally mimics that which is seen in the pupils of natural eyes.

In its intended ultimate environment, the iris device of this invention acts as a singularity, in the sense that no other device needs to be installed with it in order for it to perform its intended function. The device uniquely lends itself to very simple and very manageable insertion-into-place by the fact that it permits smoothly flowing threading of itself into an eye, generally along what can be thought of as its circular long axis, with such threading progressing from one of the "ends" that are defined in the device by the slit mentioned above. Such threading, according to the invention, takes place through an extremely small surgical incision prepared near the perimeter of the cornea. Insertion of the device is performed with little distortion of the natural tissues in the eye because of the fact that it can be threaded or snaked rotationally through such an incision, as distinguished from being bunched, gathered, folded, etc. and forced through an incision opening.

As the detailed description which now follows below is read in conjunction with the accompanying drawings, other features and advantages of the proposed device will become more fully apparent, as will also the unique installation surgical methodology which it permits.

DESCRIPTION OF THE DRAWINGS

FIG. 7 is a front elevation of an artificial iris device constructed in accordance with a preferred embodiment of the present invention.

FIG. 8 is a cross-sectional view taken generally along the line 8—8 in FIG. 7.

FIGS. 9, 10 and 11 are fragmentary cross-sectional views, each very much like what appears at the left side of FIG. 8, picturing three different modified structural forms of an artificial iris device constructed in accordance with the present invention.

FIG. 12 is a view, much like that presented in FIG. 7, showing the device of FIG. 7 somewhat "distorted" so as to produce what will be described hereinbelow as an end region overlap condition for the artificial iris device of this invention.

FIG. 13 is an enlarged, fragmentary view taken generally along the curved view-line designated 13—13 in FIG. 12.

FIG. 14 is a very simplified schematic diagram illustrating certain steps in a surgical procedure (or method) proposed by the present invention for installing an artificial iris device such as the one pictured in FIGS. 7 and 12.

FIG. 15 is a large-scale fragmentary cross-section generally taken along a line, such as line 6—6 in FIG. 5, and illustrating placement of an artificial iris device constructed in accordance with the present invention into the body of a natural eye, with the outer perimeter portions of the installed artificial iris device here being shown tucked snugly within the ciliary sulcus in the eye.

FIG. 16 is a fragmentary cross-sectional view, generally on about the same scale as that employed in FIG. 15, taken also as if along line 6—6 in FIG. 5, and illustrating placement of an artificial iris device constructed in accordance with the present invention within the capsular bag in an eye.

DETAILED DESCRIPTION OF AND BEST MODE FOR CARRYING OUT THE INVENTION

Figure 1:
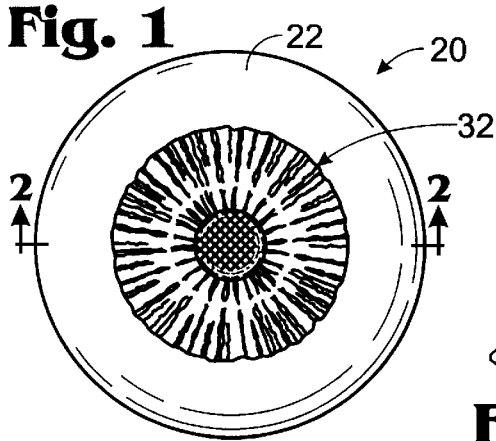
FIG. 1 is a partial front elevation of a natural eye possessing a natural, undamaged iris.
Figure 2:
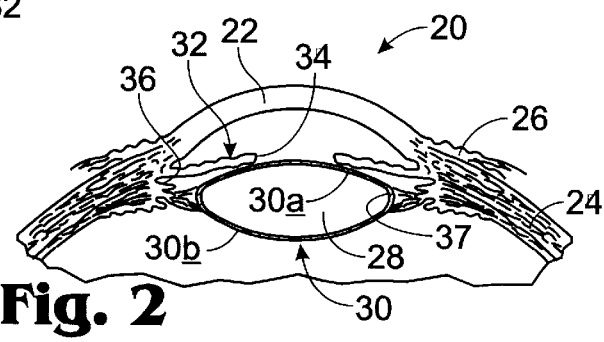
FIG. 2 is an enlarged, fragmentary cross-sectional view of a the eye shown in FIG. 1, taken generally along the line 2—2 in FIG. 1.

Turning attention now to the drawings, and referring first of all to FIGS. 1 and 2, indicated generally at 20 is a natural, undamaged eye. Eye 20 is presented in these figures with certain selected anatomical features specifically marked. The following are the marked anatomical components of this eye: the cornea 22; the sclera 24, (see particularly FIG. 2) which joins with the cornea through the limbus 26; the lens 28 which resides within the capsular bag 30 which bag has the usual anterior and posterior capsules 30a, 30b, respectively; and the iris 32, including the usual pupil 34.

Focussing specifically for a moment on FIG. 2, visible in this figure are (1) the channel-1ciliary sulcus 36 which resides behind or beneath, and perimetrally with respect to, the outside diameter of the iris, and (2) the generally circular region of joinder 37 which exists within the capsular bag in the region where the anterior and posterior capsules meet, or join. It is within one of these two last-mentioned sites (36, 37) that the device of the present invention will be installed in accordance with the present invention.

Figure 3:
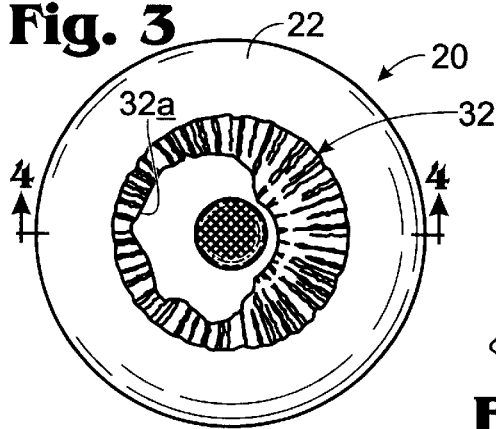
FIG. 3 is a partial, front elevation of a natural eye possessing a damaged natural iris.
Figure 4:
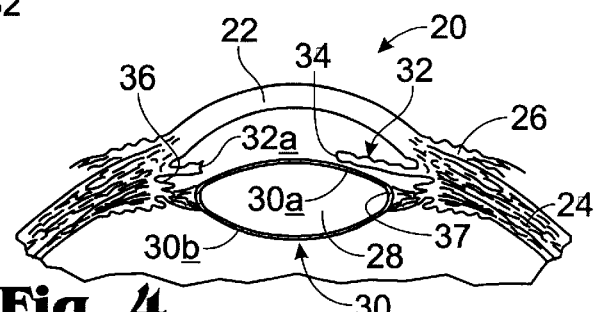
FIG. 4 is a fragmentary cross-sectional view of the eye pictured in FIG. 3, taken generally along the line 4—4 in FIG. 3.

Looking now at FIGS. 3 and 4 together, here, the very same anatomical eye components mentioned and illustrated with respect to FIGS. 1 and 2 are also present, with each bearing the same respective reference numeral. Here what is pictured is an eye which has been damaged in some fashion, and which specifically has been damaged in the iris region with the loss of iris tissue. The damaged (lost-material) iris region is indicated at 32a in FIGS. 3 and 4. As can be seen, this damaged iris region 32a is located toward the left side of the eye as such is shown in FIG. 3. The dark central circle pictured in FIG. 3 is retained in relation to the view pictured in FIG. 1 in order to illustrate the "footprint" so-to-speak of what was once a perfectly healthy and undamaged natural-iris pupil. Accordingly, the once fully defining, generally circular inside diametral edge of the iris retains only a small portion of the original pupil 34.

Figure 5:
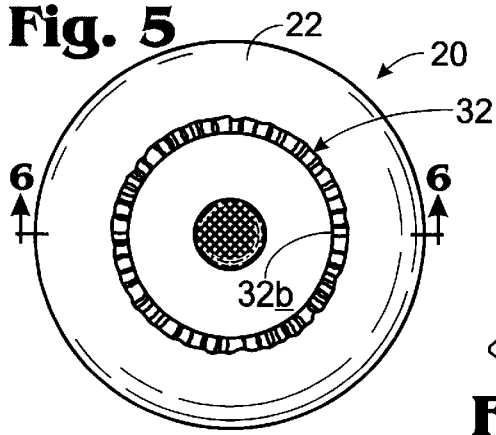
FIG. 5 is a partial front elevation of a natural eye wherein the natural iris has been surgically trimmed, in accordance with one way of practicing the present invention, to leave only a remaining annular peripheral portion.
Figure 6:
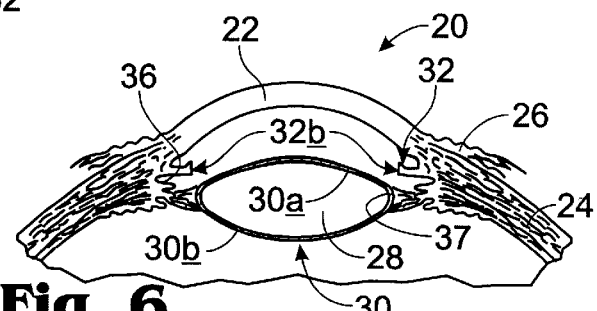
FIG. 6 is a fragmentary cross section of the eye shown in FIG. 5, taken generally along the line 6—6 in FIG. 5.

FIGS. 5 and 6 also illustrate, with the same respective reference designators employed, substantially all of the anatomical structures pictured in FIGS. 1 and 2, with the difference here being that the natural iris has been "trimmed" surgically in accordance with one way of practicing the present invention. Such trimming has been performed in order to prepare the eye for the reception of an artificial iris device constructed in accordance with the present invention. Here, the iris has been trimmed surgically to leave a relatively narrow annular peripheral portion 32b. The dark central circle in the eye pictured in FIG. 5 is retained, as was done also in FIG. 3, in order to show the footprint of what was once, but which is now completely gone, the natural pupil.

Reference should be made back to FIGS. 1–6, inclusive, in conjunction with the descriptive material which now follows.

FIGS. 7 and 8 illustrate a preferred embodiment of the present invention wherein an artificial iris device, constructed according to the invention, is shown generally at 38. This device takes the form of a thin flat annular web, or wafer, of a suitable flexible and bio-compatible material, such as a silicone material. Specifically it takes the form of an annulus of material (as pictured in FIG. 7) having a nominal inside edge diameter, $D_1$, of about 3- to about 4-millimeters, and a nominal outside edge diameter, $D_2$, of about 10- to about 11-millimeters. These inside and outside diameter characteristics are preferably substantially and smoothly circular, i.e., without any jagged discontinuities, with these edges generally, in a circular sense, paralleling what could be thought of as the circular long axis 38a in the body of device 38. Formed at one location in the body of device 38 is a slit 40 which extends radially from the axis-of-revolution symmetry axis 38b of the device. Slit 40 extends between, and opens to, the opposite (inner and outer) edges, in device 38, which edges are designated, respectively, 38c, 38d. Preferably, when device 38 is resting in what might be thought of as a nominal quiescent state (on a flat surface), for example, the portions thereof, referred to as opposite ends herein, that define opposite sides of slit 40 substantially contact one another. These opposite ends are given the reference numerals 38e, 38f in FIG. 7. The thickness of device 38, shown at T in FIG. 8, is typically about 0.1- to about 0.3-millimeters. Flexibility in the device is pictured specifically in FIG. 8 in two different curvilinearly-deflected conditions illustrated by dash-double-dot and dash-triple-dot lines, respectively, in that figure.

The dimensions selected for device 38, such as the several dimensions just mentioned above, are completely matters of surgical judgement and choice, and can be selected so as to furnish, for any particular installation operation, an appropriate fit with regard to the specific eye and eye location wherein the device is intended to be used. Further describing device 38, preferably the body of the device is suitably colored (by any appropriate technique) so as, essentially, to match the color of the damaged iris which it is intended to augment or replace. Pictured in the form of a truncated, angular wedge which is shaded at 42 in FIG. 8 is an illustration of uniform coloring which might be employed in the device. Similarly, pictured at 44 in FIG. 7 is an angular, truncated-wedge-like region in the body of device 38 which is illustrated with surface markings that are intended to show another kind of coloration modification that is usable. Specifically, this is a modification wherein that coloration is variegated, such as is the coloration in the usual natural iris. Color variegation can be created by any suitable conventional technique. Yet another consideration relating to the body of device 38, is that there may be instances where, as contrasted to having the body of the device essentially completely light-opaque, it is desirable to have this body afforded a certain amount of light transmissivity, normally preferably in the region immediately adjacent the inside diameter of the device. Such light transmissivity affords a certain degree of selective control over the way in which light is passed to the interior of the eye that receives device 38. This consideration is also a matter of surgical judgement and choice.

In relation to use of a device like device 38, if the same is selected to be used in a condition where it is to reside in place in an eye with ends 38e, 38f abutting one another, then, the dimensions of the device are selected in such a manner that inside diameter $D_1$ has the desired final diameter for an artificial pupil, and diameter $D_2$ is sized to allow snug fitment within the generally circular or annular region in the eye where installation is to take place. For example, if installation is to occur in the ciliary sulcus, then diameter $D_2$ will be chosen so that it is just about the same as, or perhaps slightly less than, the diameter of the outer perimeter of the ciliary sulcus. If, on the other hand, the device is intended to be installed in the capsular bag, then outside diameter $D_2$ is selected so that it will fit appropriately and substantially matchingly within the circular region that defines the area where the anterior capsule and the posterior capsule meet or join.

According to the present invention, a device like device 38 is intended to be installed in such a fashion that there will not be any gap, i.e., any light-passing gap, in existence between ends 38d, 38f. There may, however, be an overlap of these ends to accommodate proper fitment, or for other selected reasons, and such an overlap condition is pictured very generally in FIGS. 12 and 13. Here, device 38 can be seen to have been closed upon itself generally uniformly about axis of symmetry 38b, with ends 38e and 38f overlapping. The degree of overlap is adjustable, as is indicated by the double-ended arrow that is provided in FIG. 13.

Completing a description of what is shown on the plate of drawings now being discussed, FIGS. 9, 10 and 11 illustrate certain general structural modifications that may be desired in the configuration of device 38. In FIG. 9, a device 46 is shown which, between its inside and outside edges, has the shape pictured in cross section in FIG. 9. FIG. 10 shows a modified device 48 having, between its inner and outer circular edges, the configuration pictured here in cross section. Similarly, FIG. 11 shows a modified device 50 whose cross-sectional configuration between its inner and outer circular edges is as pictured here in cross section. Other cross-sectional configurations may of course be employed.

Focusing attention now on FIGS. 14, 15 and 16, surgical implanting and placement of the device of the present invention is performed, in accordance with this invention, in a quite unique fashion. Two surgical-placement procedures, and ultimate resident placements, for the device of the present invention, will now be generally described. Both "placements" begin with and utilize an important practice which is common to both kinds of installation. This common practice is specifically illustrated in FIG. 14.

Thus, and with reference to FIG. 14, and regardless of the final destination for a device, such as device 38, a small lateral or peripheral surgical incision, such as a linear incision, is created at one selected side of the cornea, and such an incision is shown generally at 52 in FIG. 14. This incision can be made in any suitable way by the practicing surgeon, and the incision will preferably have a relatively short length of no more than about 3-millimeters. The length of this incision preferably is just slightly greater than the radial width of the body of device 38, i.e., the dimension between inside and outside edges 38c, 38d.

With incision 52 prepared, and through suitable instrument manipulation by techniques well known to ophthalmic surgeons, device 38 is introduced in the inside of the eye through incision 52 by threading, or snaking, the device, generally as is illustrated by arrow 54 in FIG. 14. In particular, the device is threaded gently and smoothly through incision 52 in a circular or rotating fashion, generally turning the device on and along what has been referred to as its long circular axis 38a, and progressing from a single end, such as end 38f, in the device. As introduction of the device occurs in this manner, one will appreciate that very little distortion of the corneal tissue in the region of incision 52 is required because of the "snaking in" manner of installation which is uniquely promoted by device 38. Smooth-flowing insertion is especially accommodated by the fact, in particular, that the inner and outer circular edges are smooth and continuous and without any jagged discontinuities.

With the device inserted, as just generally described, beneath the cornea, and through suitable conventional manipulation techniques, the surgeon now rotates the device, generally as suggested by arrow 56 in FIG. 14, to place it in the precise location and angular orientation which has been selected for installation.

FIG. 15 illustrates a circumstance and condition where device 38 has been selected for insertion in a condition with its outer circular edge received within the ciliary sulcus, with the former iris, as pictured in this figure, having been trimmed in accordance with what is pictured in FIGS. 5 and 6 (such trimming being, of course, a matter of surgical judgment based, inter alia, upon an informed appraisal of the ongoing viability of any remaining, undamaged iris tissue).

FIG. 16 illustrates the result of the placement of device 38 within the capsular bag, wherein there has been prepared an appropriate central opening, such as that shown at 58 in FIG. 16. This is a placement procedure which will be employed typically under circumstances where, for example, the eye simultaneously receives, or has previously received, an artificial lens, such as that pictured generally at 60 in FIG. 16. In this condition, device 38 is disposed within the capsular bag, immediately underneath the rimming annular portion of the anterior capsule, with the outer circular edge of device 38 seated within the capsular bag in the region of joinder 37 between the anterior and posterior capsules. Such placement not only securely seats the device in place, but also takes advantage of the device's placement here to act as an important physical separator between the anterior and posterior capsules at this perimeter location.

In both of the installations just described, it will often be the case that no suturing is required, principally because of the fact that slit 52 can be so tiny. Also, in both kinds of installation procedures, and as has already been suggested, it will not absolutely be necessary to trim the damaged natural iris to a condition like that shown in FIG. 5. Rather, if the iris is at least partially functional after its damage, it can be left, for example, in a condition like that pictured in FIG. 3, with the artificial iris device of the invention simply supplementing (augmenting) the remaining portions of the natural iris.

The device of this invention, and the surgical procedure which it permits to be performed, thus offer a number of very important advantages and advances in the state of the art. The device itself is of extremely simple construction, and is unitary (i.e., it requires nothing other than itself to be installed for it to work properly). It uniquely lends itself to gentle (and only modestly disruptive) surgical insertion practice in the form of threading it and passing it gently and confidently through a tiny slit such, as slit 52, in the cornea. Once in place, and assuming that size determinations have been properly made, if any angular rotation were ever to occur in the device relative to its seat within the body of the eye, the opposite "ends" of the device will not part to expose a light-passing gap. The device is uniquely suited for selective placement either in the realm of the ciliary sulcus or in the realm of the inside of the capsular bag.

Coloration of the device will result in it having a quite natural appearance in its final setting, particularly if color variegation is employed. The introduction of a certain permitted amount of light transmissivity in the region of the artificial pupil which the iris device offers, allows an opportunity for the surgeon to control to a certain extent the postoperative light-receptive characteristics of the eye.

These and other various advantages which are proposed by the structure, and by the methodology of the present invention, and taking into account the several kinds of structural modifications which have been shown and suggested herein, will become readily apparent to those skilled in the art, and definitively form an important part of the present invention.

What is claimed is:

1. A single-piece artificial, implantable iris device designed for placement in a subject's eye to replace, at least partially, the natural iris in that eye, said device comprising an elongate, generally annular body formed of a thin expanse of an at least partially light-blocking material, and having an axis of revolution symmetry, and inner and outer, generally circular, different-radius edges, including a larger radius edge and a smaller radius edge, that generally centrally circumsurround the axis, and a single, generally radially disposed slit in the body extending in the body's expanse material between, and opening to, each of said edges, and defining a pair adjacent ends in said body, said edges, throughout their respective length, following generally substantially non-deviating circular paths, and said expanse material substantially completely spanning the area bounded by said edges and said ends.

2. The device of claim 1, wherein said slit extends nominally along a straight line which is a radial line relative to said axis.

3. The device of claims 1 or 2, wherein said body is colored in a manner which substantially matches the color of the natural iris which the device is intended at least partially to replace.

4. The device of claims 1 or 2, wherein said body is variegatedly colored in a manner which substantially matches the variegated color of the natural iris which the device is intended at least partially to replace.

5. A method of implanting an artificial, implantable iris device designed for use in a subject's eye to replace, at least partially, the natural iris in that eye, where the device takes the form of a single, thin and flexible annular body defined by a thin expanse of a light-blocking material, and having (1) inner and outer, generally circular inner and outer edges that generally circularly parallel a generally circular long axis in the body, and (2) a generally radially extending slit that extends between and opens to both edges to define opposite ends of the material in the body, and where the expanse material substantially span the area bounded by the body's edges and ends, said method comprising preparing a peripheral incision in the cornea in the selected subject's eye, thus to afford mechanical access to a selected placement region in the interior of the eye, inserting the device into the eye interior by rotationally threading the device, along its generally circular long axis, through the prepared incision, and progressing from one of the device's body's opposite ends, and locating, and rotationally orienting, the inserted device within the selected placement region in the eye to position it with a desired orientation in that region.

6. The method of claim 5, wherein the selected placement region is the ciliary sulcus in the eye, and said inserting and orienting steps lead to positioning of the device with its outer edge tucked within the ciliary sulcus.

7. The method of claim 5, wherein the selected placement region is beneath the anterior capsule of the capsular bag in the eye, and wherein the method further includes preparing an access opening through the anterior capsule, and wherein, further, said inserting and orienting steps lead to positioning of the device with its outer edge tucked within the capsular bag in the region where the anterior and posterior capsules meet.

8. The method of claim 7, wherein device placement performs the further step of physically separating the anterior and posterior capsules in the region of meeting therebetween.

* * * * *